United States Patent [19]
Pollock

[11] Patent Number: 6,110,966
[45] Date of Patent: Aug. 29, 2000

[54] TRIPLE ACTION COMPLEX

[75] Inventor: David E. Pollock, St. Pete Beach, Fla.

[73] Assignee: Medi-Cell Laboratories, Inc., Forth Worth, Tex.

[21] Appl. No.: 09/252,478

[22] Filed: Feb. 18, 1999

Related U.S. Application Data

[60] Provisional application No. 60/075,432, Feb. 20, 1998.

[51] Int. Cl.$^7$ ..................................................... A61K 31/34
[52] U.S. Cl. .......................... 514/474; 514/459; 514/557
[58] Field of Search ...................................... 514/474, 459, 514/557; 424/59, 422, 401

[56] References Cited

U.S. PATENT DOCUMENTS

| | | |
|---|---|---|
| 2,377,188 | 5/1945 | Schwenk et al. . |
| 4,590,067 | 5/1986 | Meisner . |
| 4,647,453 | 3/1987 | Meisner . |
| 4,670,263 | 6/1987 | Noorlander . |
| 4,695,452 | 9/1987 | Gannis et al. . |
| 4,772,591 | 9/1988 | Meisner . |
| 4,818,521 | 4/1989 | Tamabuchi . |
| 4,919,921 | 4/1990 | Hatae . |
| 4,938,969 | 7/1990 | Schinitsky et al. . |
| 4,975,272 | 12/1990 | Voyt . |
| 4,983,382 | 1/1991 | Wilmott et al. . |
| 5,021,452 | 6/1991 | Labbé et al. . |
| 5,091,171 | 2/1992 | Yu et al. . |
| 5,140,043 | 8/1992 | Darr et al. ............................... 514/474 |
| 5,376,361 | 12/1994 | Perricone . |
| 5,391,373 | 2/1995 | Mausner . |
| 5,470,874 | 11/1995 | Lerner . |
| 5,516,793 | 5/1996 | Duffy . |
| 5,574,063 | 11/1996 | Perricone . |
| 5,654,336 | 8/1997 | Yu et al. . |
| 5,698,206 | 12/1997 | Becker et al. .......................... 424/401 |
| 5,703,122 | 12/1997 | Duffy ...................................... 514/474 |
| 5,709,868 | 1/1998 | Perricone . |
| 5,709,873 | 1/1998 | Bar-Shalom et al. ................... 424/422 |
| 5,843,411 | 12/1998 | Hernandez et al. ....................... 424/59 |
| 5,885,974 | 3/1999 | Danielov ................................ 514/109 |
| 5,891,452 | 4/1999 | Sebillote-Arnaud et al. .......... 424/401 |

FOREIGN PATENT DOCUMENTS

| | | |
|---|---|---|
| 821967 | 2/1998 | European Pat. Off. ....... A61K 35/78 |
| 2744976 | 4/1979 | Germany . |
| 45-23634 | 8/1970 | Japan . |
| 51-73137 | 6/1976 | Japan . |
| 56-120612 | 9/1981 | Japan . |
| 60-116616 | 6/1985 | Japan . |
| 60-116618 | 6/1985 | Japan . |
| 61-152613 | 7/1986 | Japan . |
| 468628 | 10/1973 | U.S.S.R. . |

OTHER PUBLICATIONS

J.C. Murray, "Photoprotection of Human Skin by Topical Vitamin C", *Clinical Research*, vol. 40, No. 2, 1992, p. 143A.

"Ascorbyl Glucoseamine™ Advanced Vitamin C", Collaborative Laboratories Product Profile, 8 pages, Jan. 8, 1998.

G. Block, "The Data Support a Role for Antioxidants in Reducing Cancer Risk", *Nutrition Reviews*, vol. 50, No. 7, Jul. 1992, pp. 207–213.

R.A. Jacobs, et al., "Immunocompetence and Oxidant Defense During Ascorbate Depletion of Healthy Men", *Am J Clin Nutr*, 1991;54:1302S–9S.

G.A. Meadows, et al., "Ascorbate in the Treatment of Experimental Transplanted Melanoma", *Am J Clin Nutr*, 1991;54:1284S–91S.

K. Repinsky, "Invisible Skin Shields", *Longevity*, Mar. 1992, p. 14.

K. Griffith, "New Retin–A Rival no Rx Needed", *Longevity*, Jun. 1992, p. 32.

"Rub on Vitamin C and Rub Out Small Wrinkles", Product Promotional Brochure, Anti–Aging International, 1992.

R. Wilson, "Antioxidants to Augment the Efficacy of Sunscreens", *Drugs & Cosmetic Industry*, pp. 32, 34, 38,and 68, Aug. 1992.

N.V. Perricone "The Photoprotective and Anti–Imflammatory Effects of Topical Ascorbyl Palmitate", *J Geriatric Dermatology*, vol. 1, No. 1, pp. 5–10, Spring 1993.

P. Wolf et al., "Effect of Sunscreens on UV Radiation–Induced Enhancement of Melanoma Growth in Mice", *J National Cancer Institute*, vol. 86, No. 2, Jan. 19, 1994, pp. 99–105.

Modern Cosmeticology vol. 1, Sunburn and Sun–tan Preparations, *The Principles and Practice of Modern Cosmetics*, pp. 197–200, 204, 215, 219–221.

K.C. Smart, et al., "Effect of Ascorbic Acid and its Synthetic Lipophilic Derivative Ascorbyl Palmitate on Phorbol Ester––induced Skin–tumor Promotion in Mice", *Am J Clin Nutri*, 1991; 54:1266S–1273S.

*Primary Examiner*—William R. A. Jarvis
*Assistant Examiner*—Vicki Kim
*Attorney, Agent, or Firm*—Banner & Witcoff, Ltd.

[57] ABSTRACT

A triple action complex containing three forms of vitamin C which provides the triple action of a major anti-oxidant, an anti-inflammatory and a collagen booster. The triple action complex contains ascorbic acid, sodium ascorbate, and ascorbyl glucosamine as the three forms of vitamin C, an alpha and/or beta hydroxy acid, sea kelp, glycerin, 1,3 butylene glycol, sodium hydroxide and water.

11 Claims, No Drawings

TRIPLE ACTION COMPLEX

This application is a continuation in part of prior U.S. provisional application Ser. No. 60/075,432, filed Feb. 20, 1998.

BACKGROUND OF THE INVENTION

1. Field of the Invention

The present invention relates to a triple action complex containing three types of vitamin C that is used for treatment of the skin.

2. Discussion of the Prior Art

There have been a variety of substances that have been used to improve skin appearance. Efforts have been made to not only improve the appearance of the outer (visible) skin but also to rejuvenate and reclaim elasticity and/or suppleness lost from aging and sun and/or promote collagen synthesis, and/or to prevent oxidative damages, and/or prevent UV damage due to exposure to sunlight and weather. There have also been efforts to treat skin ailments such as acne, eczema, and the like with topical formulations. The use of vitamin C (ascorbic acid) and its derivatives are compounds which have been topically applied as an active ingredient for the treatment of various skin conditions. Vitamin C helps to stimulate and regulate the production of collagen in human skin tissue thus retarding the formation of wrinkles and providing a healthier more youthful appearance. Vitamin C also acts to help prevent or minimize lipid oxidation and other forms of cellular damage resulting from exposure to the suns ultraviolet rays.

Alpha hydroxy acids, such as glycolic acids, lactic acids, and malic acids, are known to improve certain skin disorders such as dry skin, dandruff, keratoses, age spots, wrinkles, ichthyosis, eczema and acne. They is also useful for healing photo damaged skin. U.S. Pat. No. 5,091,171, for example, provides amphoteric compositions comprising alpha hydroxy acids and related compounds. U.S. Pat. Nos. 5,516,793 and 5,703,122 disclose skin treating compositions comprising the use of ascorbic acid compositions to reduce irritation of the topically applied active ingredients. The active ingredient may be an alpha hydroxy such as glycolic acid.

U.S. Pat. No. 5,376,361 relates to a composition for topical application to the skin comprising vitamin E, as well as reductants including alpha hydroxy acids, ascorbic acids and fat soluble fatty acids esters of ascorbic acid. U.S. Pat. No. 5,470,874 provides a therapeutic composition for topical application comprising as therapeutic components ascorbic acid and proanthocyanidine compounds.

U.S. Pat. No. 5,574,063 also teaches the use of vitamin E in combination with alpha hydroxy acids particularly glycolic acids for topical application to the skin. In addition to the active ingredients, ascorbic acid or a fatty acid ester thereof is also employed in the composition. U.S. Pat. No. 5,709,868 relates to the use of lipoic acid in topical compositions. The composition also includes a fatty acid ester of ascorbic acid as well as an alpha hydroxy such as glycolic acid.

With these and other known ingredients, end-users may suffer from irritation or dermatitis due to the active ingredient, the vehicle, or a combination of both. High concentrations of glycolic acid (e.g. 10%), for example, are effective for treating certain skin disorders, but can cause significant irritation at these concentrations, including tingling, itching, burning, redness, and peeling. Such irritation is, of course, undesirable. Not only does the irritation provide discomfort, it may also give the skin a non-aesthetic appearance.

It is also known that when a formulation contains an alpha hydroxy acid and a metallic alkali such as sodium hydroxide, the composition becomes therapeutically ineffective. Reasons for such loss are discussed in U. S. Pat. No. 5,091,171. Thus it has been undesirable to add sodium hydroxide to such skin formulations to increase the pH.

It is desirable to obtain a product which contains vitamin C and an alpha and/or beta hydroxy acid that does not irritate the skin upon use.

SUMMARY OF THE INVENTION

It is an object of the present invention to provide a topically applied skin care agent which eliminates or reduces the occurrence of irritation which may accompany treatment of a skin condition.

It is an object of the present invention to provide a topically applied skin care agent which contains three types of vitamin C and an alpha and/or beta hydroxy acid.

Another object of the present invention is to provide a triple action complex that provides the triple action of a major anti-oxidant, an anti-inflammatory and a collagen booster.

It is a further object of the present invention to provide a topically applied skin care agent that contains sodium hydroxide to adjust the pH of the agent.

It is an object of the present invention to provide a topically applied skin care which combines an alpha and/or beta hydroxy acid with sodium hydroxide without reducing therapeutic effects of the alpha and/or beta hydroxy acid.

It is a further object of the present invention to provide a topically applied skin care agent with improved efficacy.

Applicants discovered that the combination of three types of vitamin C, an alpha and/or beta hydroxy acid such as glycolic acid, sea kelp, glycerin, 1,3 butylene glycol, sodium hydroxide and water provides an effective composition for treatment of the skin.

The present invention also provides a skin care agent which does not itself irritate the skin when topically administered to the patient

DETAILED DESCRIPTION OF THE PREFERRED EMBODIMENTS

The present invention is directed to a triple action complex containing three types of vitamin C which can be used in a variety of skin care compositions. Vitamin C provides the triple action of a major anti-oxidant, an anti-inflammatory and a collagen booster. Clinical studies have found that Vitamin C assists in smoothing away wrinkles, by acting as an anti-oxidant and neutralizing oxygen free radicals that occur naturally. Vitamin C also boosts collagen levels by stimulating fibroblasts for a more youthful appearance. Vitamin C will also improve skin clarity by balancing and minimizing the darkening of pigment in the skin and protect against the signs of aging by shielding the skin from UV light.

The triple action complex of the present invention also contains an alpha and/or beta hydroxy acid, sea kelp, glycerin, 1,3 butylene glycol, sodium hydroxide and water.

The three types of vitamin C used in the present invention are ascorbic acid, sodium ascorbate, and ascorbyl glucosamine, a polyamine complex.

The ascorbic acid is preferably incorporated into 1,3 butylene glycol prior to addition to the composition. The amount of ascorbic acid is between about 0.5 and 30 wt % based on the total composition, preferably between about 0.5 and 15, more preferably between about 1 and 10 wt % and most preferably about 2 wt %. The amount of 1,3 butylene glycol is less than 15 wt %, preferably about 10 wt %.

Alternatively, the ascorbic acid may be encapsulated in lecithin. The encapsulation protects the ascorbic acid from reacting with sodium hydroxide. The amount of lecithin is less than 1 wt % lecithin The amount of sodium ascorbate is between about 0.5 and 30 wt % based on the total composition, preferably between about 0.5 and 15, more preferably between about 1 and 10 wt % and most preferably about 4 wt %.

The amount of ascorbyl glucosamine is between about 1 and 75 wt %, preferably, between about 5 and 18 wt % based on the total composition, more preferably between about 8 and 15 wt %, and most preferably about 12 wt %. Ascorbyl glycosamine is a water soluble polyamine complex produced from ascorbic acid and polyglucosamine wherein the ascorbic acid portion of the complex is protected and has antioxidant and anti-collagenase properties.

The alpha and/or beta hydroxy acid helps skin maintain moisture and exfoliates away dead cells. Suitable alpha hydroxy acids, and related acids such as beta hydroxy acids, generally have two to six carbon atoms. Examples include glycolic acid, lactic acid, citric acid, malic acid, tartaric acid, glycuronic acid, pyruvic acid 2-hydroxyisobutyric acid, 3-hydroxybutyric acid, salicylic acid, and derivatives thereof, such as esters and reverse esters with alcohols having one to six carbon atoms (e.g., methyl pyruvate). The preferred alpha hydroxy acid is glycolic acid.

The amount of alpha and/or beta hydroxy acid is between about 1 and 75 wt %, preferably between about 10 and 45 wt % based on the total composition, more preferably between about 25 and 35 wt %, and most preferably about 32 wt %. The alpha and beta hydroxy acids may be used in combination to provide the indicated amounts.

Sodium hydroxide is added in an amount effective to obtain a pH of about 2.5 to 6.5, preferably about 4.0 to 4.5. The amount of sodium hydroxide is between about 5 and 35 wt %, preferably, between about 10 and 25 wt % based on the total weight of the composition, preferably between about 14 and 22 wt %, most preferably about 18 wt %.

Sea kelp is added in an effective amount to catalyze the active ingredients and to counteract the irritation of the acids. The amount of sea kelp is between about 5 and 15 wt % based on the total weight of the composition, preferably between about 7 and 12 wt %, and most preferably about 10 wt %.

Glycerine is a humectant and a solvent for the active ingredients. Glycerine is added in an amount of between about 2 and 8 wt % based on the total weight of the composition, preferably about 3 and 6 wt %, and most preferably about 4 wt %. Water is added to bring the composition to 100%.

The mixture is prepared by combining all of the ingredients. Preferably the ascorbic acid (dissolved in 1,3 butylene glycol), and sodium ascorbate, are combined with water. Then glycolic acid and sodium hydroxide are mixed together and added to the solution. Finally, the glycerine and ascorbyl glucosamine are combined and added to the solution. The pH is adjusted by the addition of sodium hydroxide or ascorbic acid. Sea kelp is added either prior to the addition of glucosamine or at the end after pH adjustment.

A preferred embodiment combines:

|  | wt % |
| --- | --- |
| Ascorbic Acid | 18 |
| Lecithin | <10 |
| Sodium Ascorbate | 2 |
| Sea Kelp | 10 |
| Glycolic Acid | 32 |
| Sodium hydroxide | 18 |
| Glycerine | 4 |
| Ascorbyl Glucosamine | 12 |
| Water | balance |

The triple action complex aids in reducing fine lines and wrinkles, evens out skin tones and provides an overall improved appearance. The triple action complex can be used by itself as a potent intensive skin complex agent or it can be incorporated into formulations which are used for topical application to the skin.

The triple action complex of the present invention can be added to various skin care compositions to enhance therapeutic effects of those compositions. Generally the triple action complex is added to such compositions in amounts between about 0.01 and 100 wt %, preferably about 5 to 25 wt %. Suitable skin care compositions include intensive cell therapy compositions, moisturizers, eye treatments and masks, hand and body creams, lotions, acne products, skin care bars, soaps bars and liquids, toilet water, and hand treatment compositions. Other compositions can use the triple action complex in amounts up to 80% such in a dermal patch or an intensive serum.

The skin care compositions may contain other vitamins such as vitamin A, vitamin E, and vitamin B6, and other ingredients such as aloe vera and botanical blends. The skin care compositions may also include conventional adjuvants, such as viscosity modifying agents, preservatives, humectants, demulcents, moisturizers, colorants, fragrances and compatible mixtures thereof Exemplary viscosity modifying agents include, but are not limited to, xanthan gum, hydroxylpropyl cellulose and/or carboxymethyl cellulose. Preservatives may be included as readily available and well known in the art.

The skin care compositions may also include a dispersant for one or more of the components, such as a colorant or fragrance. Suitable dispersants include various polyhydric alcohol anhydride partial higher fatty acid ester, e.g., Span 20, sorbitan monolaurate; Span 40, sorbitan monopalmitate; Span 60, sorbitan monostearate; Span 65, sorbitan tristearate; Span 80, sorbitan monooleate; Span 85, sorbitan trioleate or similar compounds, including Tween 20, sorbitan monolaurate polyoxyalkylene; Tween 40, sorbitan monopalmitate polyoxyalkylene, Tween 65, polyoxyethylene sorbitan tristearate, Tween 80, and the like.

Suitable inert vehicles can be used in the compositions such as simple solutions (e.g., isotonic saline), or emulsified mixtures including one or more components selected from water, organic solvents, oils, emulsifiers and the like. Exemplary vehicles include water (preferably distilled, deionized, or demineralized), alcohol (e.g., ethanol, isopropanol), propylene glycol, glycerin mixtures thereof as the diluent. If necessary, an emulsifier or surfactant may be used to facilitate solubilization of the triple action complex into the composition.

EXAMPLES

Example 1

Purified water (8 wt %) is combined with 2 wt % ascorbic acid, dissolved in 1,3 butylene glycol (10 wt %), and 4 wt % sodium ascorbate. After mixing, a combination of 32 wt % glycolic acid and 18 wt % sodium hydroxide is added to the combination. Then, 4 wt % glycerine is mixed with 12 wt % ascorbyl glucosamine and the mixture is slowly added to the combination and mixed. The pH is adjusted by adding sodium hydroxide or ascorbic acid to reach a final pH of 4. Sea kelp (10 wt %) is added and mixed into the composition.

What is claimed is:

1. A triple action complex for topical skin care use comprising:

about 0.5 to 30 wt % ascorbic acid;

about 0.5 to 30 wt % sodium ascorbate;

about 1 to 75 wt % ascorbyl glucosamine;

about 1 to 75 wt % alpha and/or beta hydroxy acid; and water.

2. The triple action complex of claim 1 further comprising about 2 to 8 wt % glycerine.

3. The triple action complex of claim 1 further comprising about 5 to 15 wt % sea kelp.

4. The triple action complex of claim 1 further comprising about 5 to 35 wt % sodium hydroxide.

5. A triple action complex for topical skin care use comprising:

about 0.5 to 30 wt % ascorbic acid;

<15 wt % 1,3 butylene glycol;

about 0.5 to 30 wt % sodium ascorbate;

about 5 to 18 wt % ascorbyl glucosamine;

about 10 to 45 wt % alpha and/or beta hydroxy acid;

about 2 to 8 wt % glycerine;

about 5 to 15 wt % sea kelp;

about 10 to 25 wt % sodium hydroxide; and the balance water.

6. The triple action complex of claim 5 comprising:

about 0.5 to 15 wt % ascorbic acid;

about 15 wt % 1,3 butylene glycol;

about 0.5 to 15 wt % sodium ascorbate;

about 8 to 15 wt % ascorbyl glucosamine;

about 25 to 35 wt % alpha and/or beta hydroxy acid;

about 3 to 6 wt % glycerine;

about 7 to 12 wt % sea kelp;

about 14 to 22 wt % sodium hydroxide; and the balance water.

7. The triple action complex of claim 6 comprising:

about 18 wt % ascorbic acid

<15 wt % 1,3 butylene glycol;

about 2 wt % sodium ascorbate about 10 wt % sea kelp about 32 wt % glycolic acid about 18 wt % sodium hydroxide about 4 wt % glycerine about 12 wt % ascorbyl glucosamine; and the balance water.

8. A method for treating dry skin comprising applying to the skin a moisturizer comprising the triple action complex of claim 1.

9. A method of treating acne comprising applying to the acne a composition comprising the triple action complex of claim 1.

10. A method for treating dry skin comprising applying to the skin a moisturizer comprising the triple action complex of claim 5.

11. A method of treating acne comprising applying to the acne a composition comprising the triple action complex of claim 5.

* * * * *